United States Patent [19]

Cartmell

[11] Patent Number: 4,838,273
[45] Date of Patent: Jun. 13, 1989

[54] MEDICAL ELECTRODE

[75] Inventor: James V. Cartmell, Dayton, Ohio

[73] Assignee: Baxter International Inc., Deerfield, Ill.

[21] Appl. No.: 65,277

[22] Filed: Jun. 22, 1987

Related U.S. Application Data

[60] Division of Ser. No. 608,188, May 9, 1984, Pat. No. 4,674,511, which is a continuation-in-part of Ser. No. 246,873, Mar. 23, 1981, abandoned, which is a continuation-in-part of Ser. No. 34,394, Apr. 30, 1979, Pat. No. 4,257,424.

[51] Int. Cl.⁴ .............................................. A61B 5/04
[52] U.S. Cl. .................................. 128/640; 128/798; 128/802
[58] Field of Search ........................ 128/639–641, 128/644, 798, 802, 803

[56] References Cited

U.S. PATENT DOCUMENTS

| | | | |
|---|---|---|---|
| 1,631,265 | 8/1924 | Harris . | |
| 1,777,162 | 9/1930 | Biddle . | |
| 1,959,293 | 5/1934 | Phillips | 164/42 |
| 1,973,911 | 9/1934 | Ruben . | |
| 2,230,829 | 2/1941 | Cesareo | 312/1 |
| 2,417,497 | 3/1947 | Hulslander, Sr. | 206/58 |
| 2,555,037 | 5/1951 | Jensen | 128/417 |
| 2,808,352 | 10/1957 | Coleman et al. | 117/227 |
| 2,943,627 | 4/1957 | Howell | 128/416 |
| 2,943,628 | 7/1960 | Howell | 128/418 |
| 3,027,333 | 3/1962 | Friedman | 252/521 |
| 3,101,282 | 8/1963 | Glassco et al. | 118/40 |
| 3,132,204 | 5/1964 | Giellerup | 174/117 |
| 3,151,619 | 10/1964 | Sullivan | 128/640 |
| 3,170,459 | 2/1965 | Phipps et al. | 128/640 |
| 3,173,728 | 10/1962 | Sheer | 312/73 |
| 3,283,886 | 11/1966 | Addis et al. | 206/52 |
| 3,357,930 | 12/1967 | Marks et al. . | |
| 3,368,522 | 2/1968 | Cordis | 118/43 |
| 3,435,127 | 3/1969 | Rose et al. | 174/94 |
| 3,475,213 | 10/1969 | Stow | 117/227 |
| 3,505,144 | 4/1970 | Kilduff et al. | 156/259 |
| 3,547,104 | 12/1970 | Buffington | 128/630 |
| 3,547,105 | 12/1970 | Paine | 128/206 |
| 3,565,059 | 2/1971 | Hauser et al. | 128/2.06 |
| 3,572,323 | 3/1971 | Yuan | 128/2.06 |
| 3,607,788 | 9/1971 | Adolf | 252/510 |
| 3,640,741 | 2/1972 | Etes | 106/170 |
| 3,662,745 | 5/1972 | Cosentino | 128/2 E |

(List continued on next page.)

FOREIGN PATENT DOCUMENTS

| | | | |
|---|---|---|---|
| 0143272 | 5/1985 | European Pat. Off. . | |
| 2271846 | 12/1975 | France | 128/803 |
| 6803290 | 9/1968 | Netherlands . | |
| 1299449 | 12/1972 | United Kingdom . | |
| 1441622 | 7/1976 | United Kingdom | 128/639 |
| 1499801 | 2/1978 | United Kingdom . | |
| 1519782 | 8/1978 | United Kingdom | 128/640 |

OTHER PUBLICATIONS

Neuman, "Flexible Thin Film Skin Electrodes . . . ", DIG. 10th Int. Conf. on Med. & Bio. Eng., p. 73, 1973.
"The Shape Conforming Electrode", Med. & Bio. Eng., vol. 7, pp. 341–343, 1968.
Leask et al., "A Multi-pole Printed Circuit Electrode", The Lancet, p. 1082, 5/16/64.
Mariott et al., "Improved ECG Monitoring . . . " J. Electrocardiology., vol. 10 (2), 1977, pp. 119–122.
Sullivan et al., "A Low Mass Electrode . . . ", J. Applied Psysic vol. 16, pp. 939–940, 1961.
Webster, "Flexible Electrodes", Med. Inst. App, & Design, pp. 245–247, 1978.

Primary Examiner—Lee S. Cohen
Attorney, Agent, or Firm—Roger S. Dybvig

[57] ABSTRACT

The signal conducting element of a medical electrode of the type bridged to skin by electrolyte and which may be X-ray transparent comprises a thin layer of a conductive paint adhered to a relatively thin supporting substrate, said substrate with adhered paint extending remotely from the electrolyte-to-skin interface for circuit connection. The electrolyte may be loaded in a sponge engaging the paint or may be in a conductive adhesive layer applied to the substrate. The electrode may also have a second and more aggressive adhesive for skin attachment. A method for producing assemblies of interconnected electrodes is also described.

6 Claims, 7 Drawing Sheets

U.S. PATENT DOCUMENTS

| | | | |
|---|---|---|---|
| 3,665,064 | 5/1972 | Mosier et al. | 264/104 |
| 3,674,176 | 7/1972 | Sagi | 221/135 |
| 3,720,209 | 3/1973 | Bolduc | 128/2.06 E |
| 3,746,004 | 7/1973 | Jankelson | 128/410 |
| 3,752,303 | 8/1973 | Foster | 206/52 |
| 3,762,946 | 10/1973 | Stow | 117/227 |
| 3,805,769 | 4/1974 | Sessions | 128/641 |
| 3,828,766 | 8/1974 | Krasnow | 128/2.1 E |
| 3,832,598 | 8/1974 | Oehmke et al. | 174/117 A |
| 3,834,373 | 9/1974 | Sato | 128/2.06 E |
| 3,835,992 | 9/1974 | Adams IV | 206/390 |
| 3,868,946 | 3/1975 | Hurley | 128/2.1 E |
| 3,882,853 | 5/1975 | Gofman et al. | 128/2.06 E |
| 3,888,240 | 6/1975 | Reinhold, Jr. et al. | 128/644 |
| 3,901,218 | 8/1975 | Buchalter | 128/2.06 E |
| 3,911,906 | 10/1975 | Reinhold | 128/2.06 E |
| 3,961,623 | 6/1976 | Milani | 128/2.06 E |
| 3,976,055 | 8/1976 | Monter et al. | 128/2.06 E |
| 3,977,392 | 8/1976 | Manley | 128/641 |
| 3,989,050 | 11/1976 | Buchalter | 128/419 |
| 3,993,049 | 11/1976 | Kater | 128/2.06 E |
| 3,998,215 | 12/1976 | Anderson et al. | 128/2.06 E |
| 4,002,221 | 1/1977 | Buchalter | 181/0.5 |
| 4,016,869 | 4/1977 | Reichenberger | 128/2.1 E |
| 4,026,757 | 5/1977 | Crawford | 156/575 |
| 4,029,086 | 6/1977 | Corasanti | 128/2.06 E |
| 4,040,412 | 8/1977 | Sato | 128/640 |
| 4,050,453 | 9/1977 | Castillo et al. | 128/640 |
| 4,051,842 | 10/1977 | Hazel et al. | 128/640 |
| 4,063,352 | 12/1977 | Bevilacqua | 29/630 |
| 4,066,078 | 1/1978 | Berg | 128/2.06 E |
| 4,067,342 | 1/1978 | Burton | 128/418 |
| 4,082,087 | 4/1978 | Howson | 128/640 |
| 4,102,331 | 7/1978 | Grayzel et al. | 128/640 |
| 4,112,941 | 9/1978 | Larimore | 128/2.06 E |
| 4,125,110 | 11/1978 | Hymes | 128/2.06 E |
| 4,141,366 | 2/1979 | Cross, Jr. et al. | 128/418 |
| 4,155,354 | 5/1979 | Rasmussen | 128/640 |
| 4,166,453 | 9/1979 | McClelland | 128/639 |
| 4,243,051 | 1/1981 | Wittemann | 128/798 |
| 4,243,052 | 1/1981 | Bailey | 128/798 |
| 4,257,424 | 3/1981 | Cartmell | 128/641 |
| 4,267,840 | 5/1981 | Lazar et al. | 128/303.17 |
| 4,270,544 | 6/1981 | Gilden et al. | 128/640 |
| 4,273,135 | 6/1981 | Larimore et al. | 128/640 |
| 4,274,420 | 6/1981 | Hymes | 128/641 |
| 4,300,575 | 11/1981 | Wilson | 128/798 |
| 4,319,579 | 3/1982 | Cartmell | 128/640 |
| 4,331,153 | 5/1982 | Healy | 128/641 |
| 4,352,359 | 10/1982 | Larimore et al. | 128/640 |
| 4,353,372 | 10/1982 | Ayer | 128/640 |
| 4,354,508 | 10/1982 | Murfitt et al. | 128/798 |
| 4,365,634 | 12/1982 | Bare et al. | 128/640 |
| 4,367,745 | 1/1983 | Welage | 128/303.13 |
| 4,409,981 | 10/1983 | Lundberg | 128/640 |
| 4,418,697 | 12/1983 | Tama | 128/640 |
| 4,419,091 | 12/1983 | Behl et al. | 128/803 |
| 4,539,996 | 9/1985 | Engel | 128/640 |
| 4,584,962 | 4/1986 | Cartmell | 118/43 |

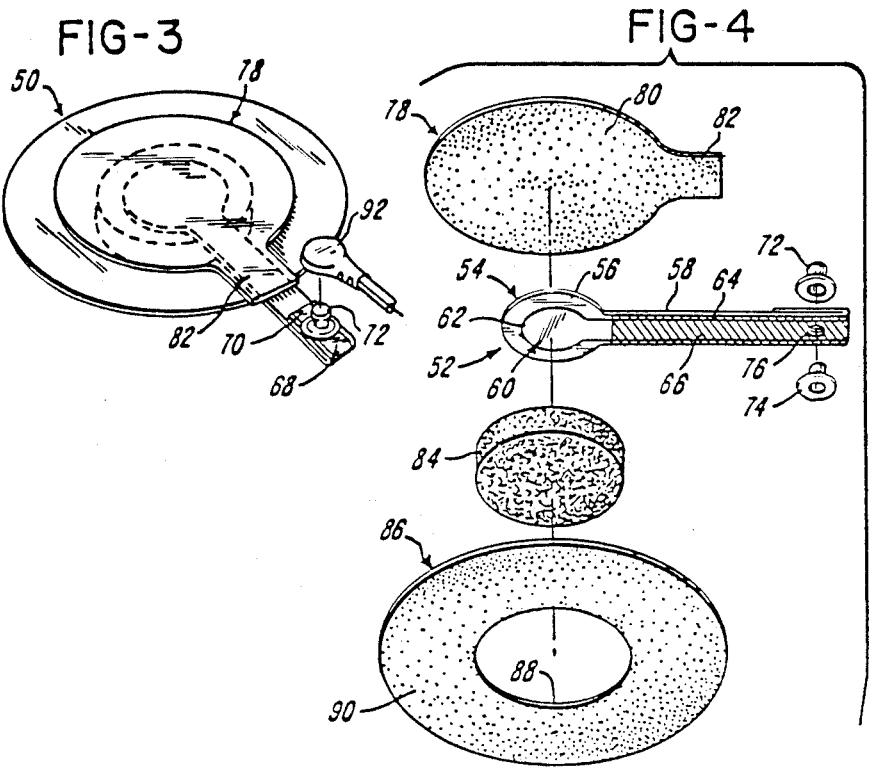
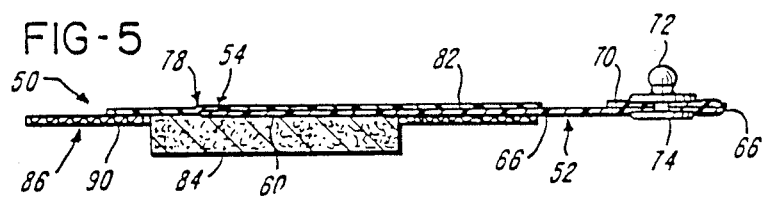

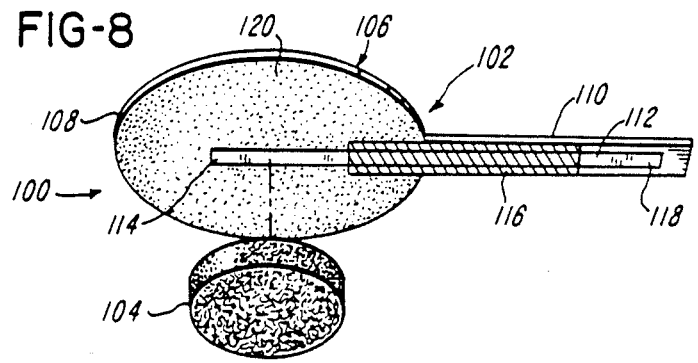
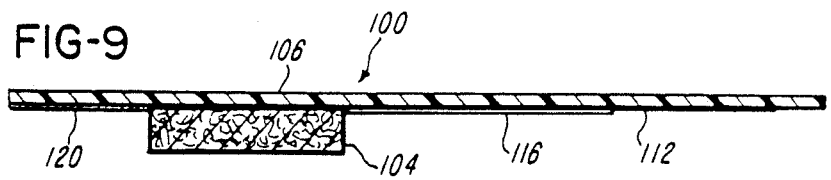
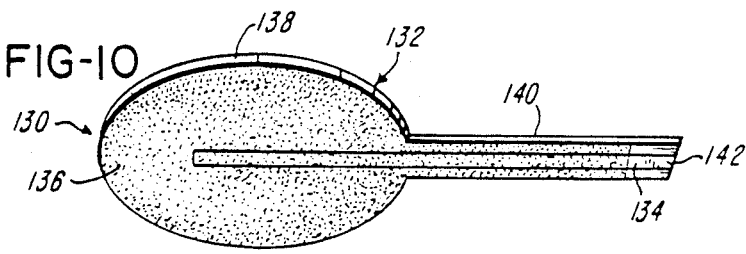
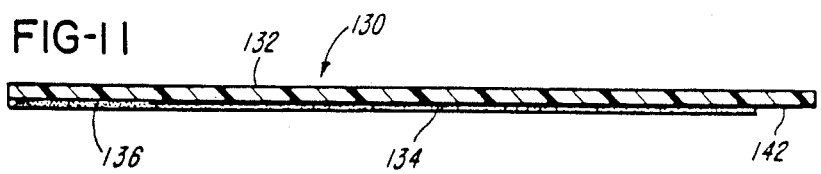

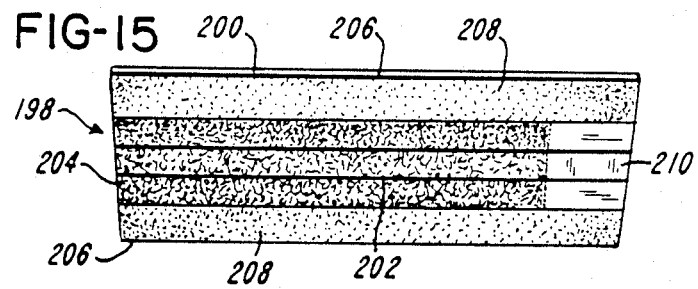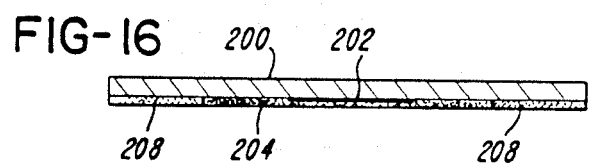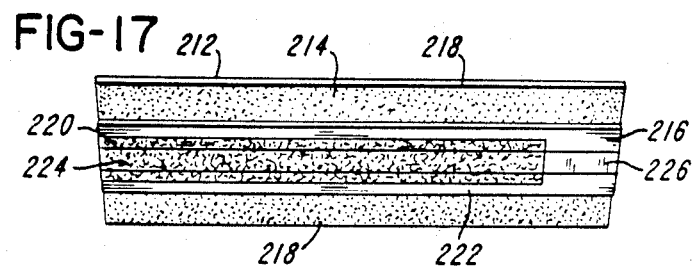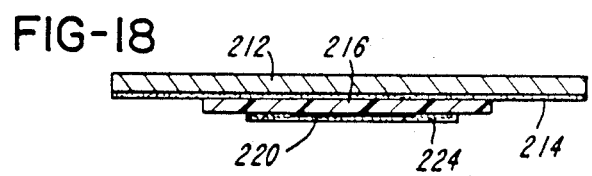

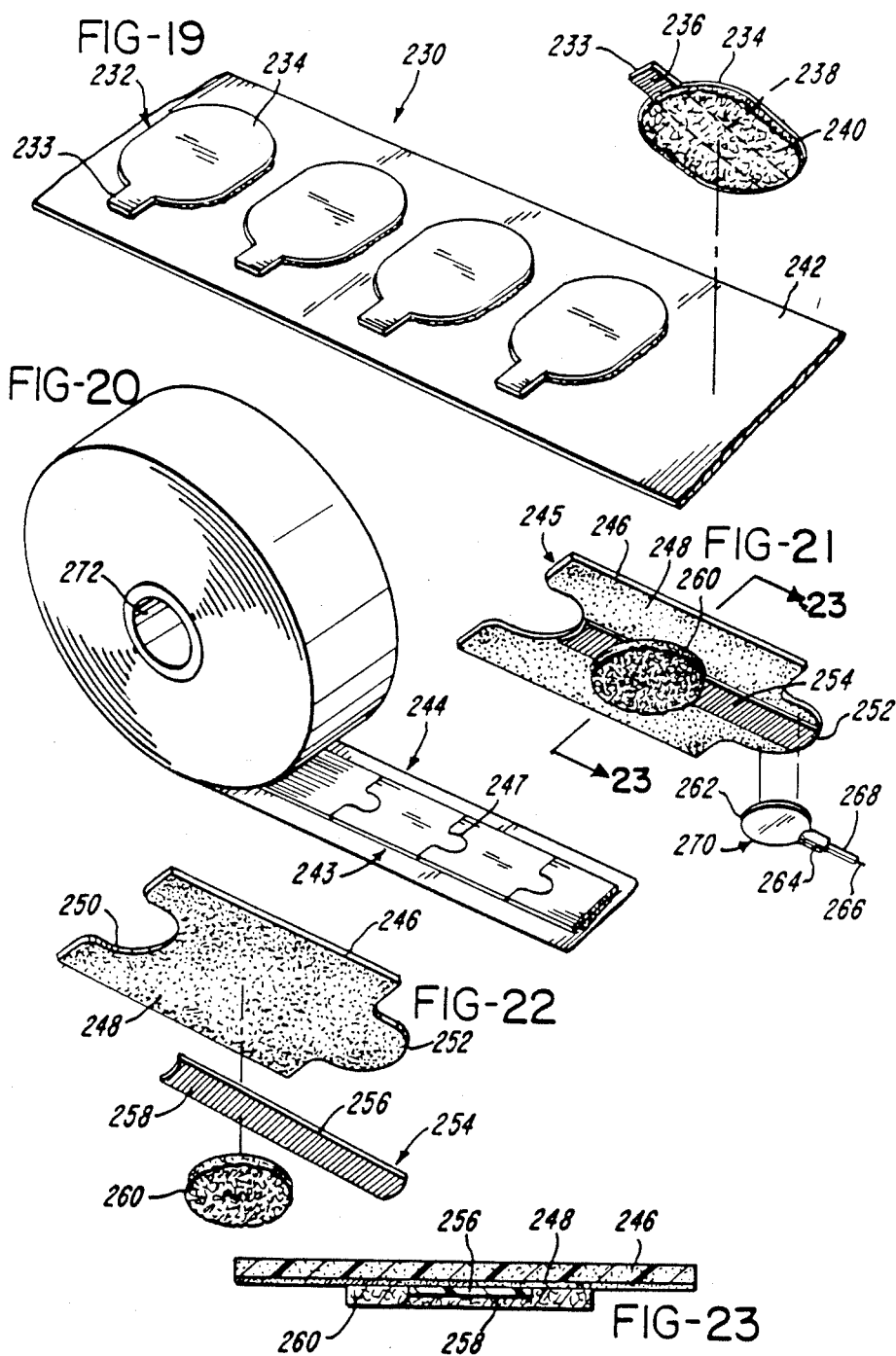

MEDICAL ELECTRODE

This is a divisional of co-pending application Ser. No. 608,188 filed on May 9, 1984, now Pat. No. 4,674,511, which is a continuation in part of application Ser. No. 246,873 filed Mar. 23, 1981, now abandoned, which was continuation in part of application Ser. No. 34,394 filed Apr. 30, 1979, now U.S. Pat. No. 4,257,424, granted Mar. 24, 1981.

BRIEF SUMMARY OF THE INVENTION

A compactly assembled medical electrode of the type contacted to the skin for electrocardiograph and like forms of monitoring or for stimulation utilizes a conductor member comprising a thin strip of nonconductive material having a thin layer of electrically conductive paintable material adhered to one face thereof. A first area of the adhered conductive material is adapted for contact by an electrolyte which is used to bridge the conductive member to the skin. A second area of the conductive material is provided for connection of the electrode to external equipment. The conductive paintable material provides a continuously conductive layer extending from the electrolyte engaging first area to the remotely disposed second area of the conductive material. The conductor member may be provided with barrier means covering a portion of the paintable conductive material between the first and second areas to limit the area of the paintable material to which the electrolyte has access and thereby minimize artifact noise attributable to migration of electrolyte to surface areas of the paintable material which have not been passivated with respect to the electrolyte. In one embodiment, an electrolyte-loaded sponge is retained in position engaged with the first area of the paintable conductive material by sandwiching of the conductor member along with the electrolyte sponge between a flexible cover disc and a flexible skin contacting pad having an aperture receiving the electrolyte sponge for presenting such sponge to the surface of live skin for stimulation or monitoring purposes. In a second embodiment, an electrolyte sponge is supported in contact with the paintable conductive material at the area thereof provided for electrolyte contact by adhesion of the sponge to a flexible cover member having an adhesive surface, said electrolyte sponge being encircled by an annulus of a flexible and breathable sheet material adhered on one face thereof to the flexible cover member and provided at the opposite face thereof with a pressure sensitive adhesive layer effective for attaching the electrode to the skin of a patient and in so doing effective to press the electrolyte loaded sponge firmly against the skin of a patient. By way of illustration, the second embodiment includes a snap fastener type conductor arrangement for convenient connection of the electrode to remote monitoring or stimulating equipment.

In a third embodiment, the electrolyte loaded sponge is retained in position by adhesion to the flexible cover member and surrounded by a ring member that is also adhered to the cover sheet. In contrast to the first two embodiments, the cover sheet functions as a patient disc, the adhesive layer thereon serving to adhere the electrode to the skin of a patient. The ring member cooperates with the cover sheet and the conductive member to form a gel cup for retaining the electrolyte on the sponge and also for providing good, relatively motion free engagement between the electrolyte sponge and the skin.

In a fourth embodiment, the conductor is shaped to include a large, circular disc portion and has a pressure sensitive adhesive layer on one surface for skin contact. An electrolyte loaded sponge is adhered by the same adhesive layer to the conductor. As in the other embodiments described above, the conductor includes an elongate, painted strip of conductive material having a continuous, insulating covering intermediate its exposed ends.

In a fifth embodiment, a medical electrode is formed from a conductor comprising a suitably formed plastic sheet having a thin layer of electrically conductive, paintable material adhered to one face thereof and a layer of conductive adhesive adhered to the same face thereof and covering a substantial area of the conductive material. The conductive adhesive is pressure sensitive and serves both as an adhesive to adhere the electrode to the skin of a patient and as an electrolyte to provide an electrical bridge between the conductive material and the skin.

In a sixth embodiment, electrodes of the type described in the fifth embodiment can be conveniently produced with a large number of integrally formed, but readily separable medical electrodes attached side by side.

In a seventh embodiment, a substrate of relatively large area is painted on one face thereof with a conductive strip of relatively small area, said conductive strip flanked by portions of an aggressive patient adhesive with there being a layer of conductive adhesive overlying the conductive paint and occupying the spaces between the flanking patient adhesive portions, such electrode being attachable to the skin of a patient by means of the patient adhesive and such skin being bridged to the conductive paint by means of the conductive adhesive.

In an eighth embodiment, a substrate is covered on one face thereof by a patient adhesive of relatively large surface area to which is centrally adhered a sheet of dimensionally stable nonconductive material, such as a plastic, supporting thereon a centrally located strip of conductive paint covered and surrounded by a layer of conductive adhesive, the conductive adhesive bridging the skin of a patient to the conductive paint as the patient adhesive is adhered to the skin of the patient.

In a ninth embodiment, a shaped substrate having an outwardly projecting tab for signal connection to remote equipment is provided with a stripe of conductive paint, one portion of which overlies said outwardly projecting tab and the remainder of which, extending longitudinally over said substrate, is covered by a conductive adhesive conveniently referred to as a hydrogel adhesive. Because the hydrogel adhesive can have a tendency to creep or wander during storage, the hydrogel adhesive is protected by a release paper which extends outwardly beyond the margins of the hydrogel adhesive.

In a tenth embodiment, a plurality of electrodes resembling jigsaw puzzle pieces are interfitted tongue to opening as a continuous ribbon of separable electrodes. Each of the electrodes comprises a substrate having the jigsaw puzzle shape and coated on one face by a patient adhesive to which is mounted a relatively narrow sheet of dimensionally stable plastic material extending from tongue to opening of the jigsaw puzzle shaped sheet and carrying on an exposed face thereof a continuous stripe of electrically conductive paint. By design, the tongue is wider than the relatively narrow dimensionally stable plastic so as to leave exposed adhesive areas for adhering a signal connector to the tongue in overlying and signal conducting relationship to the conductive paint on the dimensionally stable plastic. A deposit of the aforementioned hydrogel lying over the conductive paint on the dimensionally stable plastic sheet and lapping onto the patient adhesive provides a bridge for transferring signals from the skin of a patient to the conductive paint and from the conductive paint to the aforementioned connector. The jigsaw shaped pieces arranged in the described separable ribbon assembly are conveniently adhered to an oversized continuous release paper which allows the electrode ribbons to be conveniently stored as in a roll form.

BRIEF DESCRIPTION OF THE DRAWINGS

FIG. 3 is a perspective illustration of a second embodiment.

FIG. 4 is an exploded perspective view of the second embodiment.

FIG. 5 is a vertical section of the second embodiment.

FIG. 8 is an exploded perspective view of a fourth embodiment.

FIG. 9 is a vertical section of the fourth embodiment.

FIG. 10 is a perspective view of a fifth embodiment.

FIG. 11 is a vertical section of the fifth embodiment.

FIG. 15 is a perspective illustration of a seventh embodiment.

FIG. 16 is an enlarged transverse sectional view of the embodiment in FIG. 15.

FIG. 17 is a perspective illustration of an eighth embodiment.

FIG. 18 is an enlarged transverse sectional view of the embodiment shown in FIG. 17.

FIG. 19 is a perspective illustration, with a portion exploded away, illustrating an assembly of electrodes in accordance with the ninth embodiment.

FIG. 20 is a perspective illustration, with a portion broken away, illustrating a roll of electrodes in accordance with the tenth embodiment.

FIG. 21 is a perspective illustration, with a connector exploded away, of a single electrode in accordance with the tenth embodiment.

FIG. 22 is a perspective view illustrating further exploding of the single electrode appearing in FIG. 21.

FIG. 23 is an enlarged transverse sectional view taken substantially along the line 23—23 of FIG. 21.

DETAILED DESCRIPTION

Figure 1:
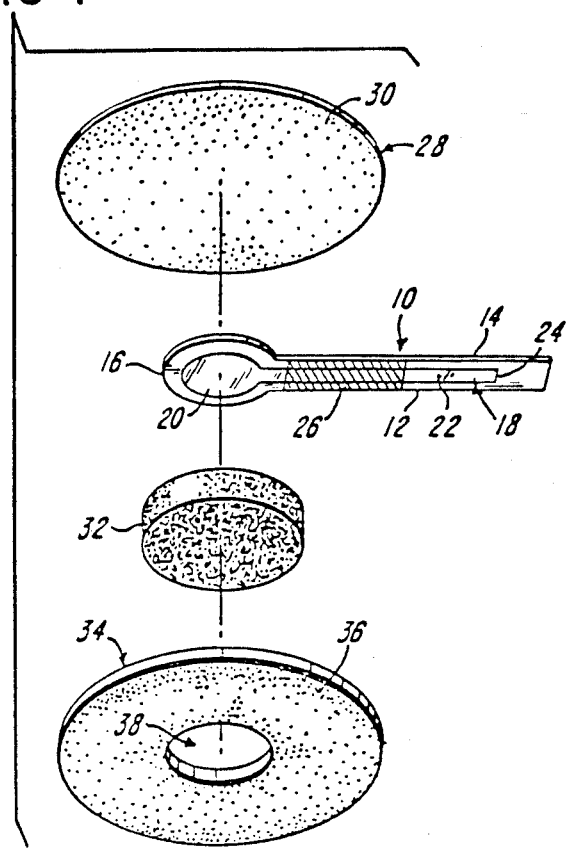
FIG. 1 is an exploded perspective view of an electrode structure in accordance with the present invention.
Figure 2:
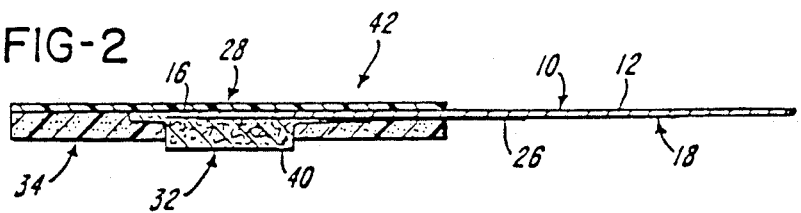
FIG. 2 is a vertical section view of the electrode structure of FIG. 1 after the assembly thereof.

Having reference to FIGS. 1 and 2, a preferred embodiment includes a signal conductor 10 which comprises a flexible, dimensionally stable, substrate 12 of a nonconductive plastic sheet material such as polyethylene terephthalate. The substrate is shaped as by die stamping to have an elongated stick portion 14 terminating at one end of the stick portion with an enlarged circular island 16. Applied to this nonconductive substrate is an electrically conductive surface layer 18, the boundaries of which are spaced inwardly from the side edges of the nonconductive substrate. The surface layer 18 thus has a circular terminal portion 20 smaller than the island 16 and, extending outwardly from the terminal portion 20 along the stick portion 14, a longitudinally disposed conductive finger 22.

The surface layer 18 comprises a layer of silver paint which is preferably applied by silk screening. As an example, the silver paint may be DuPont Conductor Composition No. 9793, a conductive paint tailored for screen printing electrical circuits onto plastic substrates. This Composition is commercially available from the DuPont Chemical Corporation. While silk screening of a commercially available compound is preferred for the formation of the conductive surface layer 18, it is to be understood that other procedures for preparation of the surface layer 18, such as brush painting, or printing, or spraying through a suitable mask may also be utilized in the practice of the present invention.

For reasons to be described, a nonconductive moisture impermeable barrier layer 26 comprising an acrylic plastic or the like is applied over the conductive surface layer 18 at that portion of the conductive finger 22 which is adjacent the terminal portion 20.

After the described preparation, the face of the signal conductor 10 which is opposite the face bearing the conductive layer 18 is pressed against an adhesive layer 30 supported by a circular plastic disc 28. The disc 28 which is preferably relatively impermeable to moisture may be a pliant plastic, such as a vinyl plastic. The exposed face of the circular island 16, together with the exposed face of the circular terminal portion 20 are then contacted by a circularly formed sponge 32. The sponge 32 is larger in diameter than the island 16 and smaller in diameter than the disc 28. The sponge 32 is retained in position by a circularly formed flexible, resilient and nonconductive foam plastic sheet or pad 34 pressed against the adhesive layer 30 so as to sandwich the sponge 32 and the signal conductor 10 between the disc 28 and the pad 34.

The pad 34 can be seen to have an adhesive layer 36 on one face thereof and a centrally located aperture 38 which is smaller in diameter than the sponge 32. Accordingly, as the pad 34 is pressed against the disc 28, the outer margin of the sponge 32 is compressed while the central portion of the sponge 32 is displaced outwardly through the aperture 38 so as to produce a pad portion 40 projecting outwardly from the adhesive coated face of the foam plastic pad 34.

It will be noted that as the pad 34 is pressed firmly against the adhesive layer 30 contained on the disc 28, the signal conductor 10 is securely positioned by reason of the back surface of the substrate 12 being adhesively engaged to the adhesive layer 30 of the disc 28 and by reason of the retention of the underlying pad 34 by such adhesive layer.

The thus mounted sponge 32 is next saturated with any suitable electrolyte, it being convenient for this purpose to introduce the electrolyte into the sponge 32 with aid of an injection device, such as a hypodermic needle, not shown.

The electrode device as thus far described is illustrated in full assembly in FIG. 2 where the assembled device has been given the reference number 42. While not illustrated, the assembled device may be protected for purposes of storage and shipment by a protective cover of a type sized to underlie the entire adhesive coated area of the pad 34 and of the type containing a recessed central portion sized to accommodate the outward projection of the pad portion 40. Such protective cover would, of course, be provided with a surface engaging the adhesive layer 36 which is of a type readily stripped from the adhesive layer 36.

The electrode device as described contains a circular terminal portion 20 which comprises a silver paint in intimate contact with the electrolyte loaded sponge 32. As understood by those skilled in the art, the silver located at the surface of the silver paint will initially have a reaction to the electrolyte contacted thereto such that should the electrode then be connected to monitoring equipment an erratic signal will appear. In time, however, the silver contacted by the electrolyte will become passivated with respect to that electrolyte and a stable signal will thereafter appear on the monitor. If, however, the electrolyte should migrate to a new and thus unpassivated area of the silver paint, the signal then being monitored would again become erratic until passivation was again accomplished. In order to protect the electrode device from such signal aberration, the present invention contemplates the provision of means restricting the areas of the silver paint which are permitted to be contacted by electrolyte. Thus, FIG. 1 displays a protective barrier layer 26 overlying a portion of the finger 22 adjacent the terminal portion 20. The preferred layer 26 comprises a nonconductive plastic such as an acrylate plastic painted over the finger 22 for an appreciable area as shown in FIG. 1. Alternatively, the indicated area may be covered with a pressure sensitive adhesive capable of adhering to the confronting face of the pad 34 so as to retard electrolyte migration. As a further alternative, any nonconductive material capable of forming a dam across the finger 22 adjacent the terminal portion 20 may be used to effectively retard electrolyte migration.

The barrier layer 26 can be recognized as a device which divides the silver painted layer 18 into a first exposed portion for receiving a signal to be monitored by ionic conduction through the electrolyte and a second exposed portion for relaying the signal by electronic conduction for application to an external circuit, not shown. The first exposed portion comprises primarily the island 16, and, while it should be understood that all areas of the layer 18 participate in electronic conduction, the second exposed portion comprises the outward end 24 of the finger 22 where isolated from contact with the electrolyte. This outward end 24 provides a surface engageable by any electronic conduction means, not shown, which may be used to relay the signal remotely to the external circuit without regard to the nature of such electronic conduction means. Thus, precautions have been taken to retard access of the electrolyte to the outer end of the finger 22 and accordingly little opportunity exists for the development of signal artifacts of the type that could result from contact of the electrolyte to dissimilar metals.

Since whatever metal that might be used for remote transmission of the signal being monitored is protected from contact with electrolyte, the signal relay means may be reusable and thus may be a permanent component of the external circuit, whereas the electrode device 42 is conveniently disposable.

An advantage to the construction of the present electrode is that the outer end of the flexible stick portion 14 can be attached to whatever signal relay means is to be employed for remote transmission without inducing any pressure on the patient to whom the electrode may have been attached. Furthermore, the stick portion 14, because flexible, will not effectively transmit external forces to which the stick portion may be exposed to the terminal portion 20 and thus forces acting on the outer end of the stick portion have only a minimal effect on the interface between the electrolyte sponge 32 and the electrically conductive surface layer 18.

An important attribute of the present invention is that the layer 18, which has been described as produced by silk screening silver paint, together with the substrate 12 can be rendered sufficiently transparent to X-ray radiation that the presence of the electrode 42 on a portion of the body, such as the chest, will not be discernible when the subject being monitored is also exposed to the X-ray radiation normally used to produce a chest X-ray photograph. In the practice of the present invention, chest X ray transparency is attained if the substrate 12 comprises a layer of polyethylene terephthalate, such as sold under the trademark MYLAR, which is in the range of ½ mil (0.00127 cm) to 20 mils (0.0508 cm) in thickness and the silver paint layer applied to such substrate is in the range of ½ mil (0.00127 cm) to 6 mils (0.0152 cm) thick. Accordingly, the combined thickness of the substrate 12 and the conductive surface layer 18 can range between 1 mil (0.00254 cm) and 26 mils (0.0660 cm).

The above indicated thickness range for Mylar represents the range of thicknesses in which mylar is thought to be commercially available. As a practical matter, however, the thickness of the Mylar layer appears to be unimportant because the Mylar thickness is always small in relation to the amount of tissue also interposed in the path of the chest X-rays. Likewise, the lower thickness in the range recited for the silver paint represents the minimum thickness of silver paint that can be silk screened with commercially available equipment, and the largest thickness in the recited range is merely the maximum thickness of silver paint that can be silk screened with commercially available equipment. Thus, it is thought that thicker layers of Mylar and/or silver paint may be employed in an X-ray procedure without interference to the intended use of the resultant X-ray photograph.

It has been reported that X-ray transparency obtained through use of a vacuum deposition of silver proves to be undesirable because vacuum deposited silver is not securely retained by a substrate such as Mylar. In contrast to such report, a silver paint, such as the aforementioned DuPont Conductor Composition No. 9793, is found to provide ample adhesion between the silver paint and the described Mylar substrate. Additionally, the silver paint provides the obvious convenience and economy of a painting operation as compared to a vacuum deposition technique.

While silver paint has been described as the preferred signal conducting means for use in the present invention, those skilled in the art will appreciate that other paints such as, for example, a conductive gold paint, may be employed in lieu of the silver paint. However, the experience to date with gold paint as well as paints produced with other conductive metals is that an electrocardiograph trace recorded while using silver as the conductive metal adhered by painting to the signal conductor element 10 produces a trace of greater fidelity.

The modified electrode 50 illustrated in FIGS. 3, 4 and 5 is superficially quite similar to the electrode 42, but a number of improvements embodied in the electrode 50 warrant a thorough description of this modification. The modification includes a signal conductor 52 comprising a substrate 54 supporting a paintable layer 60 of a conductive paint which is adhered to one face of the substrate. The substrate 54 which may be similar in shape to the previously described substrate 12 is again a dimensionally stable plastic sheet such as a sheet of polyethylene terephthalate. The substrate is shaped as by stamping to have a circular island 56 located at one end of a relatively narrow and elongate stick portion 58. The electrically conductive paintable layer 60 is shaped to have a circular terminal portion 62 adhered to the aforementioned island 56 and is shaped to have an elongated finger portion 64 extending integrally outward from the terminal portion 62. The finger portion 64 extends substantially the entire length of the stick portion 58, and it can be noted that the outermost end of the stick portion has been folded back on itself to produce an exposed conductive tab 68. In particular, it can be noted in FIG. 4 that the conductive paint is located on the face of the major length of the stick portion 58 which is visible in FIG. 4 and when the stick portion is folded to form the tab 68, the conductive paint surface 70 on the tab 68 is placed behind the stick portion 58 so as to be exposed at the opposite side of the stick portion 58. The conductive tab 68 together with that part of the finger portion 64 over which the conductive tab has been folded are through perforated to form an aperture 76 for receipt of an eyelet 74 which is pressed into a stud 72. Since, as will be explained, the stud 72 is protected from electrolyte contact, this stud may be a conventional metallic snap fastener part. It is preferred, however, that the eyelet 74 be a non-metallic piece which may be molded from a plastic material such as polyethylene or polypropylene. Thus, the stud 72 which is electrically conductive bears against the exposed electrically conductive paint surface 70 residing on the tab 68. On the other hand, the eyelet 74, being a nonconductive plastic, lies harmlessly adjacent the conductive paint extending along the finger portion 64.

The face of the substrate 54 which is opposite the conductive paint layer 60 is pressed against an adhesive layer 80 applied to a pliant and relatively impermeable protective cover 78. The cover 78 which may be a vinyl plastic is generally circular in shape but departs from true circularity by reason of the presence of an outward projection 82 at the margin thereof. When the conductor member 52 is pressed against the adhesive layer 80 present on the cover 78, the conductor member is aligned lengthwise with the outward projection 82. As is evident, the length of the outward projection 82 allows the conductor member 52 to be pressed into position against the cover 78 without the adhesive present on the projection 82 contacting the exposed surface 70 of the tab 68.

As was the case with the electrode 42, it is preferred that the paintable layer 60 comprise a silver paint and, to minimize signal artifacts, it is preferable that the finger portion 64 be so protected as to prevent a migration of electrolyte to unpassivated areas of the layer 60 capable of reacting chemically with the electrolyte. Thus, as illustrated in FIG. 4, a substantial length of the finger portion 64 has been protected with a barrier layer 66. This barrier layer may comprise a coating of a nonconductive plastic material such as acrylate plastic or simply an adhesive layer capable of adhering to an annulus 86 to be applied over the conductor member 52, as will be more fully described. It is preferred that, whatever device may be used to form the barrier layer 66, the barrier layer extend from substantially the juncture between the finger portion 64 and the terminal portion 62 to substantially the fold which places the tab 68 under the stud 72. The nonconductivity of the barrier layer 66 is important for two purposes. One purpose, as already described, is to preclude a migration of electrolyte to unprotected areas of the conductive paint layer 60. The second purpose is to avoid artifact signals attributable to contact of the conductive paint layer 60 by the skin of a patient. Accordingly, the exposed face of the finger portion 64 appearing in FIG. 4 is coated with an insulating layer including the barrier layer 66 and the nonconductive eyelet 74, such insulation extending from substantially the terminal portion 62 to the fold at the tab 68. Of course, the conductive stud 72 remains exposed but has minimal access to the patient's skin as will be more fully explained.

Upon completion of the barrier layer 66, an initially dry sponge 84 whose diameter noticeably exceeds the diameter of the island 56 is pressed against the island in such a fashion that the outer peripheral portions of the sponge adhere to the adhesive layer 80 present on the cover 78. The sponge 84 is then saturated with an electrolyte. Surrounding the sponge 84 is an annulus 86 comprising a surgical tape formed of any suitable porous and thus breathable material. The annulus 86 has a central aperture 88 of a diameter adequate to surround without contacting the circular sponge 84. The annulus 86 is adhered at one face thereof to the adhesive layer 80 present on the cover 78 and is provided at the opposite face thereof with a pressure sensitive adhesive layer 90 for attachment to the skin of a patient. FIG. 3 illustrates the side of the resulting electrode 50 which will face away from the skin when attached to a patient, and as evident, the stud 72 is positioned to project away from the skin of the patient with minimal possibility of contact to the skin.

Those skilled in the art will appreciate that during periods of storage and use of the electrode 50, electrolyte applied to the sponge 84 may migrate so as to reach the interface between the annulus 86 and the barrier layer 66 with the consequence that capillary action may advance the electrolyte outwardly in the general direction of the stud 72. Those skilled in the art will further appreciate, however, that any such capillary action will be of limited effect since any outward movement of the electrolyte will terminate when the electrolyte reaches the outer periphery of the annulus 86. Thus, even though a minor amount of capillary action might occur, the extent of action is limited by the dimensions of the annulus 86 with the consequence that only a minor proportion of electrolyte will be able to migrate away from the electrolyte sponge 84.

As suggested in FIG. 3, connection of the electrode 50 to signal monitoring equipment may be conveniently made by attaching a conventional snap fastener connector 92 to the snap fastener stud 72.

Figure 6:
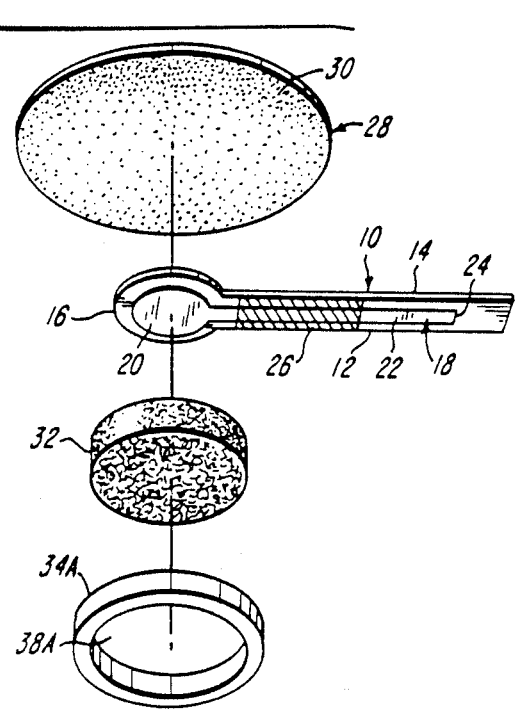
FIG. 6 is an exploded perspective view of a third embodiment.
Figure 7:
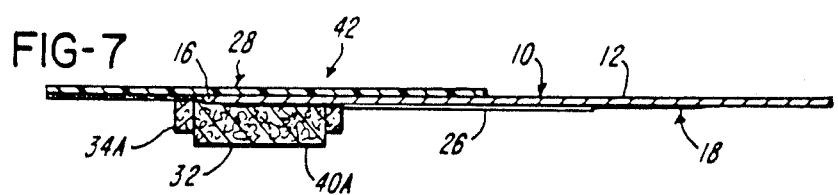
FIG. 7 is a vertical section of the third embodiment.

In the embodiment shown in FIGS. 6 and 7, the signal conductor 10, the circular plastic cover sheet or disc 28, and the circular electrolyte loaded sponge 32 may be identical to the corresponding elements shown in FIGS. 1 and 2. Accordingly, the corresponding parts are identified by the same reference numbers. Thus, the signal conductor 10 has a nonconductive substrate 12 shaped to include an elongated stick portion 14 and an enlarged circular island 16. An electrically conductive surface layer 18 having a circular terminal portion 20 and a longitudinally disposed conductive finger 22 is applied to the substrate 12. The signal conductor 10 is constructed identically to that illustrated in FIG. 1 and further description, therefore, is deemed unnecessary. The same is true of the disc 28 which is preferably made from a vinyl or other pliant, plastic material that is relatively impermeable to moisture, and it is provided with an adhesive layer 30 against which the face of the signal conductor 10 opposite the face bearing the conductive layer 18 is pressed. In the embodiment of FIGS. 6 and 7, the sponge 32, when initially dry, is coaxially aligned with and pressed against the island 16 and the adhesive layer 30 of the disc 28 so as to adhere the sponge 32 to the disc 28. The sponge 32 is thereafter saturated with an electrolyte.

After the sponge 32 is adhered to the disc 28, a ring member 34A having a central bore 38A with an inner diameter substantially identical to the outer diameter of the sponge 32 is pressed against the adhesive layer 30 and thereby adhered to the disc 28 in encircling relation to the sponge 32. The outer diameter of the ring member 34A is substantially less than the diameter of the disc 28 so that the entire ring member 34A is located completely within the margins of the disc 28 and, accordingly, is surrounded by parts of the adhesive layer 30. The height of the ring member 34A is less than the height of the sponge 32 so that, akin to embodiments described above, there is a pad portion 40A projecting outwardly beyond the skin facing surface of the ring member 34A.

The ring member 34A may be made from a relatively rigid material such as a molded polyethylene or from a highly flexible plastic such as a foamed polyethylene. In either case, the ring cooperates with the conductor 10 and the cover sheet 28 to form a cup like recess for partly confining the gel pad to better retain the electrolyte therein. And, when the electrode of FIGS. 6 and 7 is adhered to the skin of a patient, the sponge will be firmly held against the skin to reduce the opportunity for motion thereof relative to the skin that would produce artifacts.

Another feature of the embodiments of FIGS. 6 and 7 is that the adhesive layer 30 is used not only to hold the parts of electrode in assembled condition, but also to adhere the electrode to the skin of a patient so that the disc 28 in effect serves both as a cover sheet and as a patient disc.

The medical electrode, generally designated 100, shown in FIGS. 8 and 9, is of extremely simple construction and comprises an integrally formed signal conductor, generally designated 102, and a circular electrolyte loaded sponge 104.

The conductor 102 comprises a flexible, dimensionally stable substrate 106 of a nonconductive plastic sheet material such as polyethylene terephthalate. The substrate 106 is shaped as by die stamping to have an enlarged circular disc portion 108 from which extends an elongate, strip-like, stick portion 110 projecting generally radially from the periphery of the circular disc portion 108. Applied to the nonconductive substrate 106 is an electrically conductive surface layer 112 formed as an elongate strip extending along substantially the entire length and centrally of one surface of the elongate stick portion 110 and radially to the center of the disc portion 108 and then extending in a straight line past the center of the disc portion 108. Throughout its length, the boundaries of the conductive surface layer 112 are spaced inwardly from the outer margins of the nonconductive substrate 106. The conductive surface layer 112 has an inner terminal portion 114 generally centrally located with respect to the substrate disc portion 108 and which may be formed, as illustrated in FIG. 8, as a strip or ribbon of material. The shape of the terminal portion 114 is not critical, and it may be circular or have some other shape.

For reasons apparent from the description of the preceding figures, the embodiment of FIGS. 8 and 9 includes a nonconductive moisture impermeable barrier layer 116 comprising an acrylic plastic or the like applied over the conductive surface layer 112, the barrier layer 116 extending from adjacent the central terminal end 114 outwardly along the substrate stick portion 110 to a point adjacent an exposed end 118 of the conductive surface layer 112 most remote from the center of the disc portion 108.

The conductive surface layer 112 may be applied to the substrate 106 in the manner previously described with respect to the preceding embodiments. After the conductive layer 112 is formed, and either before or after the barrier layer is formed, a pressure sensitive adhesive layer 120 is applied to the same face of the substrate 106 as is the conductive surface layer 112, with the adhesive covering the entire circular disc portion 108 except for the parts thereof to which the conductive surface layer 112 and the barrier layer 116 are applied.

After completion of the entire conductor member 102, the sponge 104, when initially dry, is pressed against the center of the surface of the circular disc portion 108 to which the conductive surface layer 112 and the pressure sensitive adhesive layer 120 are applied, whereupon the sponge 104 is adhered by the adhesive layer 120 to the conductor 102. When thus assembled, the sponge 104 is located coaxially with the disc portion 108, engaging and covering the terminal end 114 of the conductive surface layer 112. Thereafter, the sponge is loaded with electrolyte.

Those familiar with the art will recognize that the embodiment of FIGS. 8 and 9 can be constructed at minimal cost and may provide a satisfactory, low cost, disposable electrode useable for many purposes. Optionally, a ring member, such as the ring member 34A, or some other member designed to assist in maintaining an electrolyte and retaining the margins of the sponge 104, may be added to the construction shown in FIGS. 8 and 9.

Referring now to FIGS. 10 and 11, another medical electrode which is also of simple construction is identified generally by the reference number 130 and comprises a single, integrally formed member comprising a nonconductive substrate 132, a conductive layer 134, and a conductive adhesive layer 136 covering the same face of the substrate 132 to which the conductive layer 134 is applied.

The substrate 132 may be identical to the previously described substrate 106 of FIGS. 8 and 9 and thus be formed with an enlarged circular disc portion 138 and a radially outwardly extending, elongate, strip-like stick portion 140. The electrically conductive surface layer 134 may be identical to the surface layer 112 of FIGS. 8 and 9, being formed as an elongate strip extending along substantially the entire length and centrally of one surface of the elongate stick portion 140 and radially to the center of the disc portion 138 and then extending in a straight line past such center. As may be observed in FIG. 10, the conductive layer 134 extends to the bitter end of the stick portion 140, whereas in FIG. 8, the conductive layer 112 terminates short of the bitter end. This is purely optional and will depend upon the type of equipment with which the electrode is designed for use or the type of connector that may be applied thereto, such as the snap fastener arrangement illustrated in FIG. 3.

Preferably, the conductive adhesive layer 136 forms a coating over the entire disc portion 138 and extends continuously from the disc portion 138 over a substantial length of the stick portion 140 and terminates at a point short of the outer terminal end, designated 142, of the conductive layer 134 to leave that end exposed for metal-to-metal contact with the connector to peripheral equipment.

Various conductive adhesive materials may be used and the material of choice will depend upon the application for which the electrode is intended. For example, if the electrode 130 is to be used as an ECG electrode, the conductive adhesive 136 could be karaya gum modified with sodium chloride. Such a composition is available in sheet form from Lectec Corporation, 120 South Crosstown Circle, Eden Prairie, Minn. Various other conductive adhesive compositions could be used. Suitable compositions are described, for example, in the following United States patents: Marks et al, U.S. Pat. No. 3,357,930; Kater, U.S. Pat. No. 3,993,049; Berg, U.S. Pat. No. 4,066,078; and Cross et al, U.S. Pat. No. 4,141,366.

Conductive adhesives available in sheet form can be applied directly to the surface of the substrate 132 over the conductive layer 134 or the conductive adhesive could be applied by spraying, silk screen, casting, or other processes.

In every case, the conductive adhesive that is used should be capable of application to the substrate 132 without adversely affecting its flexibility and must be capable of adhering to human skin upon application of pressure, either with or without a preconditioning treatment such as the application of a suitable solvent, and also must serve as an electrolyte to create an electrical bridge between the skin and the conductive layer 134.

One advantage of the electrode 130 shown in FIGS. 10 and 11 is that the electrode is applied directly to the skin without the application of an additional electrolyte which could migrate from the area of skin contact.

It should be noted that each of the embodiments shown in FIGS. 6 through 11 comprise medical electrodes that are X-ray transparent, as is the case with the embodiments shown in FIGS. 1 through 5. The preferred construction of the substrates in each case is identical, that is, the preferred material is polyethylene terephthalate, such as sold under the trademark MYLAR having a thickness in the range of ½ mil (0.00127 cm) to 20 mils (0.0508 cm). Also, the electrically conductive surface layer preferably comprises a silver paint layer, as described above, in the range of ½ mil (0.00127 cm) to 6 mils (0.152 cm). The thickness of the layer of adhesive in the embodiment of FIGS. 6 through 11 is not critical and will depend upon the type of adhesive being used. An adhesive layer of approximately 1 or 2 mils (0.00254 cm to 0.00508 cm) is desirable. Some conductive adhesives that may be useful to form the adhesive layer 136 of FIGS. 10 and 11 could be substantially thicker, in the range of 4 mils (0.01016 cm) up to ⅛ inch (0.3175 cm).

Figure 12:
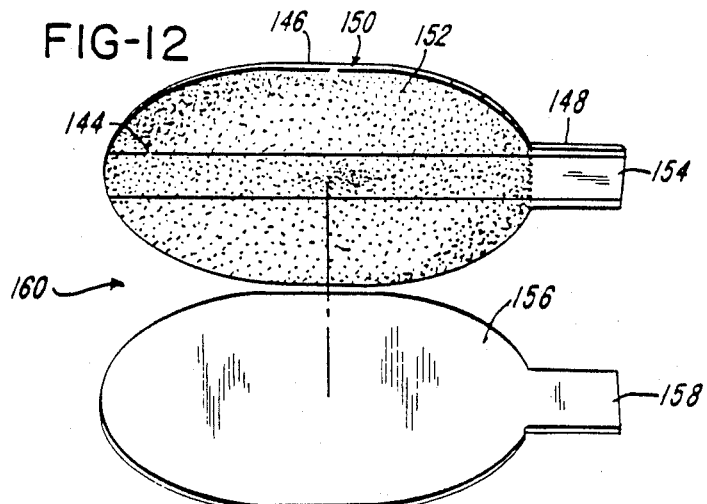
FIG. 12 is an exploded perspective view illustrating electrodes in accordance with the sixth embodiment.
Figure 13:
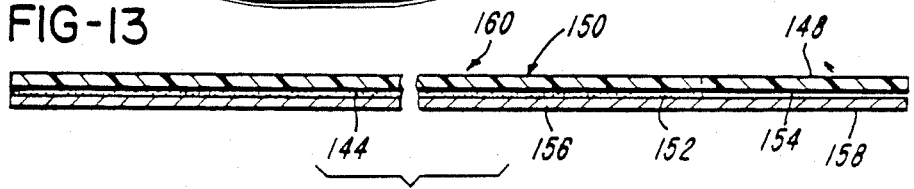
FIG. 13 is an enlarged longitudinal cross-sectional view of the embodiment in FIG. 12.

FIG. 12 illustrates a modification of the fifth embodiment wherein a paint stripe 144 is applied to a substrate 146 having an abbreviated stick portion 148 with the paint stripe 144 crossing axially an oval shaped portion 150 of the substrate to extend longitudinally over the stick portion 148. A layer of conductive adhesive 152 lies over the oval shaped portion 150 and also the paint stripe 144 within the region defined by the oval shaped portion 150; however, a portion 154 of the paint stripe 144 extending along the abbreviated stick portion 148 is free of any conductive adhesive. The conductive adhesive is protected by a somewhat oval shaped release paper 156 having an abbreviated leg portion 158 which will lie adjacent without adhering to the bare paint portion 154. The release paper is exploded away in FIG. 12 but would normally lie in intimate contact with the conductive adhesive 152, as shown in FIG. 13, with the leg portion 158 being free of any adhesive bond to the stick portion 148 or its coating of conductive paint. The resulting electrode assembly 160 requires only the peeling away of the release paper 156 to prepare the electrode for attachment to the skin of the patient and then only the attachment to the stick portion 148 of a conductor means, not shown, to electrically engage the exposed surface 154 of the paint stripe remotely from the conductive adhesive layer 152.

The embodiment of FIGS. 12 and 13 provides an exceptionally simple laminar electrode construction of a type readily produced in great quantities with simple and relatively inexpensive apparatus, not shown.

Figure 14:
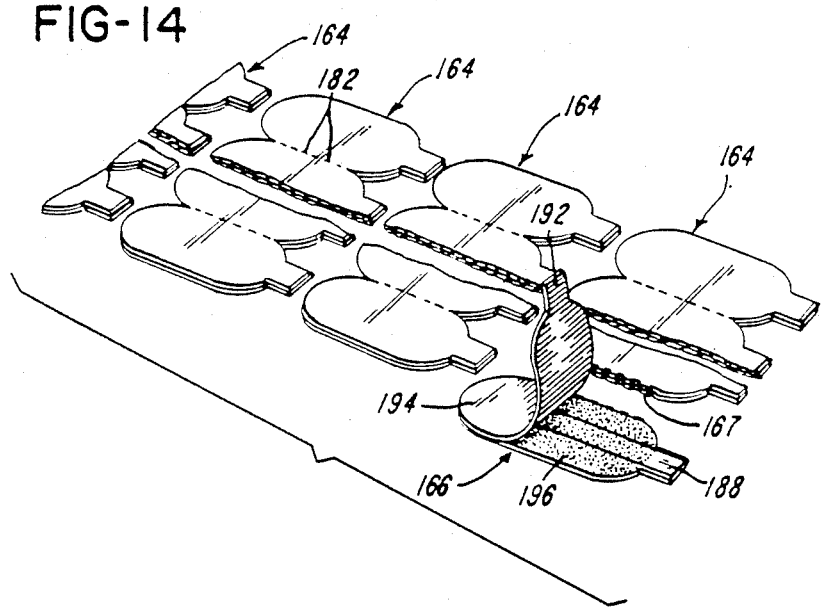
FIG. 14 is a fragmentary perspective illustration of assemblies of interconnected electrodes with portions having been broken away to illustrate the laminar construction of the electrodes and with a release paper having been peeled partially from one of the electrodes.

The electrode assemblies 160 illustrated in FIGS. 12 and 13 are cut as individual electrode laminates. As illustrated in FIG. 14, it is obviously feasible to laminate the electrodes with relatively much larger sheets supporting a plurality of side-by-side paint stripes which can then be cut by any suitable cutting mechanism to form integrally connected groups 164 containing electrode assemblies 166 which may be separated from adjacent assemblies by means of weakening lines or portions 182. The reference number 167 illustrates the tear edge resulting from separation of adjacent electrode assemblies 166. Since electrode assemblies 166 are substantially identical, except for the presence of the tear edge 167, to the electrode assemblies 160 appearing in FIGS. 12 and 13, no effort is made to more particularly describe any of the electrode assemblies 166. The reference number 188 identifies the conductive paint stripe exposed at the stick portion of the electrode assembly 166 and the reference number 196 identifies a layer of the conductive adhesive lying over most of the substrate for the electrode assembly 166 but leaving the stick portion 188 bare. The reference number 194 identifies the protective cover lightly adhered to the conductive adhesive 196, with the protective cover 194 having a tab portion 192 which lies over the stick portion 188 without having adhesive attachment thereto.

FIG. 14 illustrates a plurality of the groups 164 side by side and it is immediately apparent that a large number of the groups 164 may be cut from relatively much larger laminations than appear in FIG. 14 with only a minimal wastage of the laminate material.

An important consequence of the utilization of this invention is that integrally connected but readily separable medical electrode assemblies 166 are produced. Since the tabs 192 are not adhesively attached to the stick portions 188, the tabs are readily lifted by one's fingers to initiate removal of the protective cover 194 of release paper prior to the attachment of the uncovered electrode to a patient. Depending on the conductive adhesive being utilized, the removal of the release cover may be followed by an application of a solvent or the like for promoting adhesion of the conductive adhesive to the skin of a patient.

The electrode devices described in reference to FIGS. 10, 12 and 14 utilize a conductive adhesive compound which is duofunctional in that the same compound is used to provide an electrolyte for ionic signal conduction and to provide an adhesive surface layer for adhesion of the electrode to the skin of the patient. This duofunctional adhesive characteristic based on the current state-of-the-art is found suitable for short-term usage but is less suitable for long-term usage. Thus, the use of the adhesive compound as a carrier for the electrolyte diminishes the aggressiveness with which the resulting adhesive compound will cling to the patient's skin. Since conductive adhesive electrodes do not require any application of saline solution or the like to the patient's skin at the time the patient is being prepared for EKG examination or the like, there are many applications for the conductive adhesive electrodes described in this application in which the conductive adhesive is desired to be used despite the compromise as to adhesive aggressiveness. Nevertheless, there is a need for conductive adhesive electrodes supplemented by a more aggressive adhesive, herein called a patient adhesive, which adapts the conductive adhesive electrode for long-term usage.

FIGS. 15 and 16 illustrate a conductive adhesive electrode 198 wherein an elongate strip of substrate 200, which may be papertape, polyethylene terephthalate, or the like, is painted centrally on one face thereof with a conductive stripe 202, which is preferably a stripe of silver paint, then overpainted with a layer of conductive adhesive 204, the layer 204 being broader than the stripe 202, but not so broad as the papertape 200, thus providing margins 206 at the outside edges of the tape 200. The margins 206 each support a layer 208 of a commonly available medical grade pressure sensitive adhesive which is more aggressive than the conductive adhesive 204.

An electrode of the type illustrated in FIGS. 15 and 16 is provided with an exposed conductive portion 210 serving the same function as the exposed paint stripe 154 described in regard to the electrode structure of FIG. 12. This exposed conductive portion 210 may be engaged by snap fastener parts such as illustrated in FIG. 4. In lieu of snap fastener parts, staples, clips, or the like, may be employed for the purpose of electrode connection to peripheral equipment. Thus, in all embodiments described in this application, there is preserved a bare portion of the electrode conductor for electrical engagement to the peripheral equipment at a region where no electrolyte is available to form a half cell between metal of the electrode conductor and the metal of the lead wire connecting to the peripheral equipment.

Another manner of supplementing a conductive adhesive electrode with a more aggressive patient adhesive is illustrated in FIGS. 17 and 18 wherein the reference number 212 identifies a substrate such as a paper tape substrate and the reference number 214 identifies a pressure sensitive patient adhesive adhered to and entirely covering one surface of the substrate 212. The substrate 212 is, of course, a relatively narrow strip having an indefinite length. Adhered centrally to the exposed surface of the patient adhesive and extending longitudinally the entire length of the substrate 212 is a thin carrier sheet 216 of a flexible and dimensionally stable material such as polyethylene terephthalate. The width of the sheet 216 is less than the width of the substrate 212 so as to leave to each side of the sheet 216 a margin 218 comprising the more aggressive patient adhesive. Applied longitudinally and centrally to the lower face of the sheet 216 is a stripe 220 of a conductive paint. The stripe 220 is narrower than the sheet 216 so that margins 222 remain on the sheet 216 for receiving a layer 224 of conductive adhesive which fully covers the conductive stripe 220 and also shields the side edges of such stripe.

In use, the conductive adhesive 224 contains therein the electrolyte necessary to bridge conductive stripe 220 to the skin of a patient and the patient adhesive 214 has the aggressiveness to prolong skin attachment by the electrode for long periods. The conductive stripe 220 has a connector portion 226 which is permitted to project outwardly from the overlying conductive adhesive, thus to preserve a surface of bare conductor for engagement by a lead wire connecting to the peripheral equipment. Those skilled in the art will appreciate that the thicknesses of the several layers comprising the modified electrode of FIGS. 17 and 18 have been greatly exaggerated, the overall electrode thickness, including even the substrate, not ordinarily exceeding 10 mils.

The ninth embodiment illustrated in FIG. 19 comprises an electrode 232 structurally similar to the electrode described in reference to FIG. 12 and also structurally similar to the electrodes 166 illustrated in FIG. 14. Thus, the electrode comprises a substrate 234 which is of oblong shape with there being a tab 233 projecting outwardly from one end of the substrate. A stripe 238 of conductive paint 236, which may be a silver paint, is centrally and longitudinally applied to one face of the substrate 234 with the stripe 238 extending onto the tab 233 such that exposed silver paint resides on one face of the tab 233.

Applied to the substrate 234 in overlying relation to the paint stripe 238 is a conductive adhesive hydrogel 240. As known to those skilled in the art, the hydrogel is a gelatinous compound filled with water. Due to the gelatinous character of the conductive adhesive, the adhesive has a sufficient body to retain its own shape during short-time intervals, such as a few minutes or hours, but over long periods of time, such as normally involved in the storage and shipment of medical electrodes, the adhesive has a tendency to creep, such tendency being viscosity dependent. Since the conductive adhesive may wander or creep during storage, it is found convenient to store electrodes utilizing this type of conductive adhesive on a release paper 242, which is clearly larger than the individual electrodes placed thereon. Thus, FIG. 19 illustrates an electrode assembly 230 comprising a plurality of five electrodes placed side by side on the release paper 242 with there being a sufficient space between adjacent electrodes that the hydrogel adhesive lying between one electrode and its release paper is not apt to creep into admixture with the hydrogel of an adjacent electrode.

FIGS. 20, 21, 22 and 23 illustrate a tenth embodiment of the present invention. Electrodes 245 in this embodiment comprise substrates 246 which are shaped to have a tongue 252 at one end thereof, sized to interfit an opening 250 cut out from the opposite end thereof. The electrodes 245 may be conveniently cut from a continuous ribbon 243 of such electrodes by means of shaped incisions 247 such as appear in FIG. 20.

Entirely coating one face of the ribbon 243 is a layer of patient adhesive 248. Extending longitudinally and centrally about the ribbon 243 is a relatively narrow sheet 256 of a dimensionally stable plastic such as polyethylene terephthalate. This relatively narrow sheet 256 is adhered on one face by the patient adhesive 248 and the opposite face of the relatively narrow sheet 256 is painted with a layer of a conductive paint 258, such as the aforementioned DuPont Conductor Composition No. 9793. At the time the incisions 247 are cut through the ribbon 243, the relatively narrow sheet 256 is also cut.

Either before or after forming the incisions 247, the ribbon 243 will have placed thereon deposits 260 of the described hydrogel. These deposits are applied at a time when the hydrogel is not fully gelled and thus, when the deposits are made, the gel has an opportunity to flow outwardly and onto the adhesive 248 as appears clearly in FIG. 21. The deposits 260 may be applied in synchronization with the machinery that forms the incisions 247 so that each deposit 260 is located relatively close to each opening 250 and relatively remote from each tongue 252 as clearly appears in FIG. 22.

After allowing a sufficient opportunity for the deposited hydrogel to set so as to hold its own shape, the electrode ribbon 243 is laid against a release paper 244 in such fashion that the hydrogel deposits are sandwiched between the substrates 246 and the release paper 244, with the conductor element 254 sandwiched between the hydrogel 260 and the adhesive 248.

As is evident in FIG. 21, the conductor element 254 is narrow in relation to the width of each of the tongues 252, thus on each side of the tongues 252 there remain exposed patches of the adhesive 248 which flank the conductor element 254.

The electrodes are used by peeling individual electrodes 245, one by one, from the release paper 244, then contacting the exposed patient adhesive flanking the conductor element 254 with a conductor 262 which may have a socket 264 for receiving the insulation 268 surrounding a wire conductor 266. The conductor 262, socket 264, insulation 268, and wire 266 comprise a connector 270 for connection of any of the electrodes 245 to peripheral equipment which may be either stimulating or monitoring equipment. In use, the hydrogel deposit 260 is contacted to the skin of the patient. The adjacent patient adhesive 248 is, at the same time, pressed against the skin of the patient to reinforce the adhesive attachment of the electrode 245 to the skin of the patient. Signal connection to the peripheral equipment is made by affixing the connector 270 to the tongue 252 where it overlies and contacts the conductor element 254. The signal path thus proceeds from the patient's skin through the hydrogel deposit 260 through the conductor element 254 to the connector 270.

One of the advantages of the described electrode ribbon 243 protected by the described release paper 244 is that the electrode ribbon can be conveniently wound in roll form on suitable spools 272 such as appear in FIG. 20, and because the deposits 260 are sealed by the release paper engaging the patient adhesive 248, electrode dry-out is minimized.

Those skilled in the art will appreciate that the resulting construction of the electrode 245 is comparable to the construction of the electrode described in relation to FIGS. 17 and 18. Thus, the sectional configuration appearing in FIG. 18 bears many similarities to the sectional configuration illustrated in FIG. 23.

Paper and polyethylene terephthalate have been mentioned as suitable materials for the substrates or carrier sheets to which the conductive paint is applied. They include those elements identified by reference numbers 12, 54, 106, 132, 146, 200, 216, 234 and 256. Other materials which are flexible and substantially dimensionally stable in sheet form could be used. Another example of such material is a non-woven polyethylene material that is commercially available under the trademark TYVEK. Other substrates such as element numbers 28, 78, 212, and 246, which are adhered to the painted substrates, could be made from the same materials or could be made from resilient materials such as closed cell foamed polyethelene.

For each embodiment, a suitable cover may be provided for maintaining the electrode ready for use after shipping and storage. Any exposed adhesive coatings are preferably covered by release papers or the like, such as described in regard to the embodiment of FIGS. 12 and 14, and, desirably, the electrodes would be packaged either individually or in bulk in aluminum foil wrappers.

The electrodes of this invention are each highly x-ray transparent and could be used for monitoring applications requiring x-ray transparency. They may also be used in other monitoring applications and may be used to apply signals to the skin, such as for stimulation purposes.

Although the preferred embodiments of this invention have been described, it will be understood that various changes may be made within the scope of the appended claims.

Having thus described my invention, I claim:

1. A disposable medical electrode assembly comprising a plurality of medical electrodes aligned to form a ribbon of said medical electrodes, each medical electrode comprising a substrate having a tongue at one end thereof and a corresponding opening at the opposite end thereof, said tongue of the one of said substrates at one end of said ribbon projecting therefrom and said tongue of each of the others of said substrates interfitting said corresponding opening of an adjacent substrate, each substrate coated on one face thereof with a first adhesive layer, each electrode having a strip of plastic material adhered to said first adhesive layer, each strip having a paintable conductive layer on the face of said strip facing away from said first adhesive layer and each medical electrode having a deposit of conductive adhesive placed between its tongue and its corresponding opening and lying over a part of said paintable conductive layer.

2. The disposable medical electrode of claim 1 wherein said strip of plastic material extends lengthwise of said tongue and is narrower than said tongue, whereby portions of said first adhesive layer not contacted with said strip flank said strip for adhesive attachment to an electrode connector.

3. In combination, a disposable medical electrode and a conductor for connection of such electrode to peripheral equipment, said electrode comprising a substrate having a tongue portion at one end thereof and a corresponding opening at the opposite end thereof, said substrate having a first adhesive layer on one face thereof, a strip of plastic material adhered to said first adhesive layer, said strip having a paintable conductive layer on the face of said strip facing away from said first adhesive layer, said strip extending along the length of said tongue portion and being narrower than the width of said tongue portion, whereby portions of said first adhesive layer not covered by said strip flank said strip in the region of said tongue portion, said conductor engaging said flanking portions of said first adhesive layer while, simultaneously, lying in contact with said paintable conductive layer.

4. In combination, a disposable medical electrode and a conductor for connection of such electrode to peripheral equipment, said electrode comprising a substrate having a tongue portion at one end thereof and a corresponding opening at the opposite end thereof, said substrate having a first adhesive layer on one face thereof, a strip of plastic material adhered to said first adhesive layer, said strip having a paintable conductive layer on the face of said strip facing away from said first adhesive layer, said strip extending along said tongue portion, there being a portion of said adhesive layer on said tongue portion which is not covered by said strip, said conductor engaging said portion of said adhesive layer not covered by said strip and also lying against said paintable conductive layer.

5. A ribbon of disposable medical electrodes comprising a plurality of substrates, one for each of said electrodes, each of said substrates having tongue portion at one end thereof and a corresponding opening at an opposite end thereof, said tongue portion of the one of said substrates at one end of said ribbon projecting therefrom and said tongue portion of of each of the others of said substrates interfitting the corresponding opening of an adjacent substrates, said ribbon coated on one face thereof with a first adhesive layer, each said electrode having a strip of plastic material extending from its corresponding opening and longitudinally over said tongue portion with said strip adhered to said first adhesive layer, a paintable conductive layer lying on said strip, said paintable layer extending along said ribbon except at the junctions between tongue portions and corresponding openings, a deposit of conductive adhesive material on each of said strips between the tongue portion and the corresponding opening between which said strip extends, and a band of release material wider than said ribbon lying against said first adhesive layer and lying over said deposits of conductive adhesive material.

6. A roll of electrodes comprising a plurality of electrodes, each having a tongue at one end thereof and an opening at the opposite end thereof, said plurality of electrodes being arranged tongue-in-opening to form a continuous strip of said electrodes, each said electrode comprising a substrate having adhesive on one face thereof and conductive means forming a conductor on said substrate, a release paper adhered to the adhesive on said one face of each of said electrodes, said release paper extending continuously along the length of said strip and being wider than said strip, and said strip being rolled to form said roll of electrodes.

* * * * *

UNITED STATES PATENT AND TRADEMARK OFFICE
CERTIFICATE OF CORRECTION

PATENT NO. : 4,838,273

DATED : June 13, 1989

INVENTOR(S) : James V. Cartmell

It is certified that error appears in the above-identified patent and that said Letters Patent is hereby corrected as shown below:

Column 4, line 54, "on," should be --on--. Column 6, line 30, "x ray" should be --X-ray--; column 6, line 40, "mylar" should be --Mylar--. Claim 5, line 3 (column 18, line 3), "having tongue" should be --having a tongue--; claim 5, line 7 (column 18, line 7), "portion of of" should be --portion of--; claim 5, line 9 (column 18, line 9), "substrates" should be --substrate--.

Signed and Sealed this

Thirty-first Day of December, 1991

Attest:

HARRY F. MANBECK, JR.

*Attesting Officer*      *Commissioner of Patents and Trademarks*